(12) United States Patent
Steube

(10) Patent No.: US 9,066,690 B2
(45) Date of Patent: Jun. 30, 2015

(54) BLOOD COLLECTION NEEDLE ASSEMBLY

(75) Inventor: Gregory Alan Steube, St. Charles, MO (US)

(73) Assignee: Covidien LP, Mansfield, MA (US)

(*) Notice: Subject to any disclaimer, the term of this patent is extended or adjusted under 35 U.S.C. 154(b) by 979 days.

(21) Appl. No.: 12/211,885

(22) Filed: Sep. 17, 2008

(65) Prior Publication Data

US 2009/0088698 A1 Apr. 2, 2009

Related U.S. Application Data

(60) Provisional application No. 60/995,616, filed on Sep. 27, 2007.

(51) Int. Cl.
*A61B 5/15* (2006.01)
*A61M 25/06* (2006.01)

(52) U.S. Cl.
CPC .............. *A61B 5/1422* (2013.01); *A61M 25/06* (2013.01); *A61M 25/0693* (2013.01)

(58) Field of Classification Search
CPC ......................... A61M 25/0693; A61B 5/1422
USPC ....................... 604/164.08, 272; 600/576–577
See application file for complete search history.

(56) References Cited

U.S. PATENT DOCUMENTS

| | | |
|---|---|---|
| 3,382,865 A | 5/1968 | Worrall, Jr. |
| 3,448,740 A | 6/1969 | Figge |
| 3,585,984 A | 6/1971 | Buchanan |
| 3,589,363 A | 6/1971 | Banko et al. |
| 3,645,268 A | 2/1972 | Capote |
| 3,664,879 A | 5/1972 | Olsson |
| 3,780,733 A | 12/1973 | Martinez-Manzor |
| 3,817,240 A | 6/1974 | Ayres |
| 3,874,367 A | 4/1975 | Ayres |
| 3,886,930 A | 6/1975 | Ryan |
| 4,106,497 A | 8/1978 | Percarpio |
| 4,108,175 A | 8/1978 | Orton |
| 4,154,229 A | 5/1979 | Nugent |
| 4,166,450 A | 9/1979 | Abramson |
| 4,193,400 A | 3/1980 | Loveless |
| 4,207,870 A | 6/1980 | Eldridge |
| 4,269,186 A | 5/1981 | Loveless et al. |

(Continued)

FOREIGN PATENT DOCUMENTS

| | | |
|---|---|---|
| EP | 1602328 | 12/2005 |
| JP | 7-13304 | 7/1995 |
| WO | WO2005/092174 | 10/2005 |

OTHER PUBLICATIONS

International Search Report EP08164528 dated Dec. 12, 2008.

(Continued)

*Primary Examiner* — Rebecca E Eisenberg
(74) *Attorney, Agent, or Firm* — Lisa E. Winsor, Esq.

(57) ABSTRACT

Disclosed is a needle assembly for viewing flashback during a blood collection procedure. The needle assembly including a housing having a base portion defining a cavity and an extension extending distally from the base portion, the extension being of a transparent material and defining a lumen therethrough, a first cannula supported within the extension and extending distally from the extension, the first cannula having a piercing tip configured to enter a vessel, and a second cannula supported within the cavity of the base portion, wherein the second cannula is fluidly communicated with the first cannula via the lumen formed in the extension.

17 Claims, 4 Drawing Sheets

(56) References Cited

U.S. PATENT DOCUMENTS

| | | |
|---|---|---|
| 4,312,362 A | 1/1982 | Kaufman |
| 4,317,445 A | 3/1982 | Robinson |
| 4,340,068 A | 7/1982 | Kaugman |
| 4,343,305 A | 8/1982 | Bron |
| 4,398,544 A | 8/1983 | Nugent et al. |
| 4,409,990 A | 10/1983 | Mileikowsky |
| 4,412,548 A | 11/1983 | Hoch |
| 4,416,290 A | 11/1983 | Lutkowski |
| 4,416,291 A | 11/1983 | Kaugman |
| 4,418,703 A | 12/1983 | Hoch et al. |
| 4,436,098 A | 3/1984 | Kaugman |
| 4,444,203 A * | 4/1984 | Engelman ............ 600/577 |
| 4,565,545 A | 1/1986 | Suzuki |
| 4,626,240 A | 12/1986 | Edelman et al. |
| 4,679,571 A | 7/1987 | Frankel et al. |
| 4,702,260 A | 10/1987 | Wang |
| 4,763,667 A | 8/1988 | Manzo |
| 4,767,407 A | 8/1988 | Foran |
| 4,781,691 A | 11/1988 | Gross |
| 4,788,986 A | 12/1988 | Harris |
| 4,795,446 A | 1/1989 | Fecht |
| 4,808,156 A | 2/1989 | Dean |
| 4,844,089 A | 7/1989 | Roberti |
| 4,865,592 A | 9/1989 | Rycroft |
| 4,869,717 A | 9/1989 | Adair |
| 4,886,072 A | 12/1989 | Percarpio et al. |
| 4,894,052 A | 1/1990 | Crawford |
| 4,971,068 A | 11/1990 | Sahi |
| 5,030,207 A | 7/1991 | Mersch et al. |
| 5,032,116 A | 7/1991 | Peterson et al. |
| 5,033,476 A | 7/1991 | Kasai et al. |
| 5,069,225 A | 12/1991 | Okamura |
| 5,092,845 A | 3/1992 | Chang |
| 5,106,376 A | 4/1992 | Mononen et al. |
| 5,112,327 A | 5/1992 | Iinuma et al. |
| 5,120,319 A | 6/1992 | Van Heugten et al. |
| 5,122,121 A | 6/1992 | Sos et al. |
| 5,137,515 A | 8/1992 | Hogan |
| 5,137,518 A | 8/1992 | Mersch |
| 5,181,523 A | 1/1993 | Wendelborn |
| 5,201,794 A | 4/1993 | Kasai et al. |
| 5,217,025 A | 6/1993 | Okamura |
| 5,222,502 A | 6/1993 | Kurose |
| 5,242,411 A | 9/1993 | Yamamoto et al. |
| 5,290,246 A | 3/1994 | Yamamoto et al. |
| 5,295,969 A | 3/1994 | Fischell et al. |
| 5,295,974 A | 3/1994 | O'Laughlin |
| 5,295,980 A | 3/1994 | Ersek |
| 5,303,713 A | 4/1994 | Kurose |
| 5,306,259 A | 4/1994 | Fischell et al. |
| 5,312,345 A | 5/1994 | Cole |
| 5,312,376 A | 5/1994 | Van Heugten |
| 5,330,434 A | 7/1994 | McFarlane |
| 5,334,185 A | 8/1994 | Giesy et al. |
| 5,403,283 A | 4/1995 | Luther |
| 5,419,766 A | 5/1995 | Chang et al. |
| 5,450,856 A | 9/1995 | Norris |
| 5,496,281 A | 3/1996 | Krebs |
| 5,520,193 A | 5/1996 | Suzuki et al. |
| 5,531,701 A | 7/1996 | Luther |
| 5,533,988 A | 7/1996 | Dickerson et al. |
| 5,542,932 A | 8/1996 | Daugherty |
| 5,569,217 A | 10/1996 | Luther |
| 5,634,913 A | 6/1997 | Stinger |
| 5,683,370 A | 11/1997 | Luther et al. |
| 5,685,855 A | 11/1997 | Erskine |
| 5,697,914 A | 12/1997 | Brimhall |
| 5,755,701 A | 5/1998 | Sarstedt |
| 5,830,190 A | 11/1998 | Howell |
| 5,893,844 A | 4/1999 | Misawa |
| 5,913,848 A | 6/1999 | Luther et al. |
| 5,916,208 A | 6/1999 | Luther et al. |
| 5,935,108 A | 8/1999 | Katoh et al. |
| 5,984,895 A | 11/1999 | Padilla et al. |
| 6,096,006 A | 8/2000 | Sarstedt et al. |
| 6,110,160 A | 8/2000 | Farber |
| 6,156,010 A | 12/2000 | Kuracina et al. |
| 6,190,370 B1 | 2/2001 | Tsui |
| 6,203,533 B1 | 3/2001 | Ouchi |
| 6,217,527 B1 | 4/2001 | Selmon et al. |
| 6,261,263 B1 | 7/2001 | Huet et al. |
| 6,500,157 B2 | 12/2002 | Luther |
| 6,533,760 B2 | 3/2003 | Leong |
| 6,666,848 B2 | 12/2003 | Stone |
| 6,712,792 B2 | 3/2004 | Leong |
| 6,881,201 B1 | 4/2005 | Duchamp |
| 6,929,623 B2 | 8/2005 | Stone |
| 7,160,267 B2 | 1/2007 | Brown |
| 7,163,526 B2 | 1/2007 | Leong et al. |
| 7,226,432 B2 | 6/2007 | Brown |
| 7,396,343 B2 | 7/2008 | Brown |
| 2002/0004647 A1 * | 1/2002 | Leong ............ 604/168.01 |
| 2005/0245885 A1 | 11/2005 | Brown |
| 2008/0319346 A1 | 12/2008 | Crawford et al. |

OTHER PUBLICATIONS

Japanese Application No. 2008-248834 Office action dated Jul. 23, 2013, 7 pages, Japan.

Japanese Application No. 2008-248834 Office action dated Dec. 5, 2013, 10 pages, Japan.

Australian Application No. 2008224348 Office action dated Aug. 29, 2013, 6 pages, Australia.

* cited by examiner

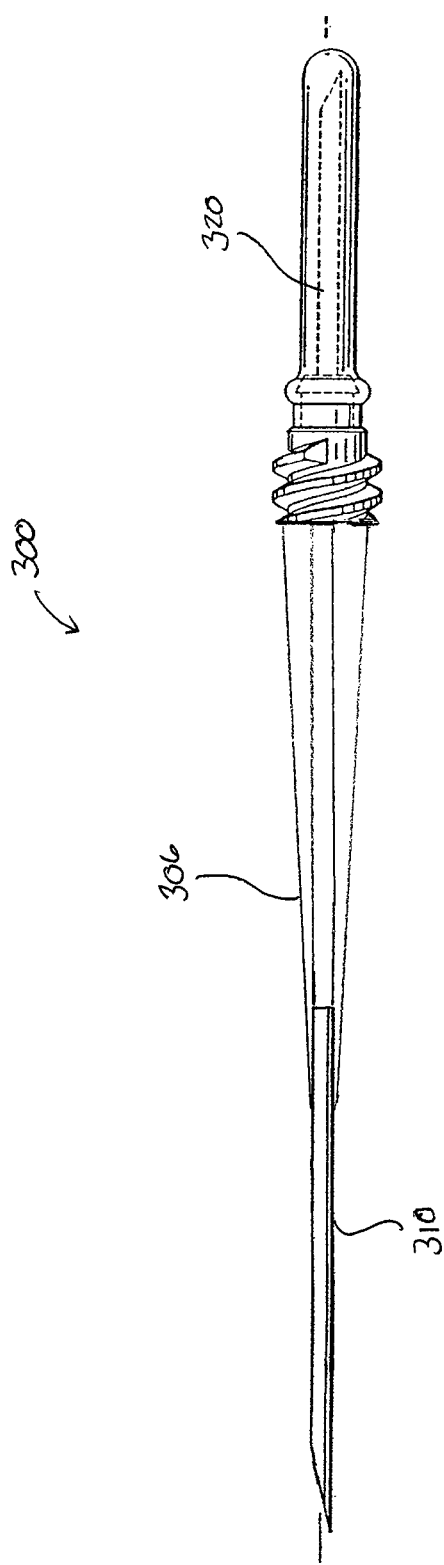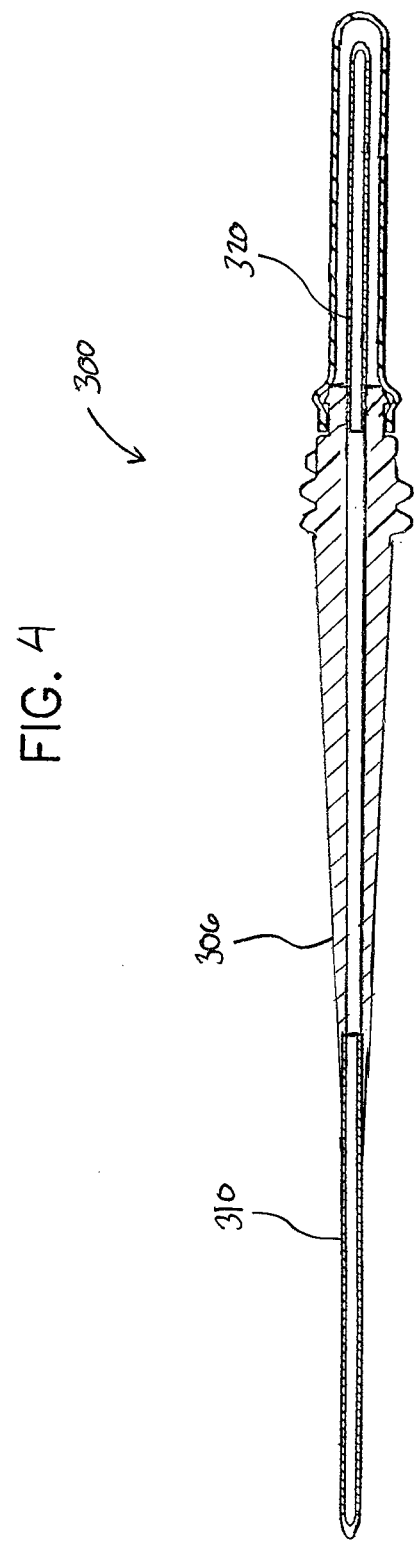
FIG. 4
FIG. 5

BLOOD COLLECTION NEEDLE ASSEMBLY

This application claims priority from U.S. Provisional Application Ser. No. 60/995,616, which was filed on Sep. 27, 2007 and is incorporated herein in its entirety by reference.

BACKGROUND

1. Technical Field

The present disclosure generally relates to phlebotomy needle assemblies and, in particular, relates to needle assemblies including extensions for visualizing "flashback".

2. Background of Related Art

Venipuncture is the primary method used for acquiring blood samples for laboratory testing. Various venipuncture devices have been developed to aid a phlebotomist in acquiring blood samples. Typically, a venipuncture device includes a needle holder having a needle that is inserted into a vein. When a vacuum tube is inserted into the needle holder, the vacuum tube begins to fill with blood confirming that the vein has been entered. During a single blood collection procedure, one or more vacuum tubes may be filled in this manner. Attempts have been made to develop improved venipuncture devices that include a "flashback" mechanism incorporated into the needle holder. These "flashback" mechanisms typically include venting structure which allows a sufficient amount of blood to enter the venipuncture device to reach a flashback chamber and, thus, allow a phlebotomist to visually confirm that a vein has been entered. However, the various venting means and/or chamber configurations permitting visualization of the "flashback" may be complicated, and therefore, expensive to manufacture. Further, in phlebotomy needle assemblies which do not have venting structure, a vacuum tube must be inserted into the needle holder before blood will flow through the needle assembly and flashback can be observed.

SUMMARY

A needle assembly for visualizing flashback prior to venting the needle assembly is provided. The needle assembly includes a housing having a base portion defining a cavity and an extension extending distally from the base portion, the extension being of a transparent material and defining a lumen therethrough. The needle assembly further includes a first cannula supported within the extension and extending distally from the extension, the first cannula having a piercing tip configured to enter a vessel and a second cannula supported within the cavity of the base portion. The second cannula is fluidly communicated with the first cannula via the lumen formed in the extension. The cavity of the base portion may be configured to receive a vacuum tube. The extension may be configured to magnify contents therein.

The needle assembly may further include an elastomeric valve operably connected to the base portion and covering the second cannula. The base portion may be integrally formed with the extension. The extension may instead be operably connected to the base portion.

The transparent extension may define a single lumen. The lumen formed in the extension defines a substantially uniform diameter along the length thereof. The extension may further define an elongated tubular body having a substantially uniform diameter along the length thereof. The extension may instead define a substantially tapered body, wherein a proximal end of the extension defines a larger diameter than a distal end thereof.

Also provided is an extension for permitting viewing of flashback prior to venting of the extension. The extension includes a substantially elongated body having proximal and distal ends and defining a first lumen therethrough. The body is constructed from a transparent material. A first cannula is operably supported on the distal end of the elongated body and defines a second lumen in fluid communication with the first lumen. A second cannula is operably supported near the proximal end of the elongated body and defines a third lumen in fluid communication with the first lumen. The first, second and third lumens may be of substantially equal diameter.

Further provided is a method of visualizing flashback during a blood collection procedure. The method includes the steps of providing a needle assembly comprising, a housing including a base portion defining a cavity and an extension extending distally from the base portion, the extension being of a transparent material and defining a lumen therethrough, a first cannula supported within the extension and extending distally from the extension, the first cannula having a piercing tip configured to enter a vessel, and a second cannula supported within the cavity of the base portion, wherein the second cannula is fluidly communicated with the first cannula via the lumen formed in the extension, and inserting the piercing tip of the first cannula into a vessel.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 4 is a side view of yet another embodiment of a needle assembly according to the present disclosure; and FIG. 5 is a side cross-sectional view of the needle assembly of FIG. 4.

DETAILED DESCRIPTION

Figure 1:
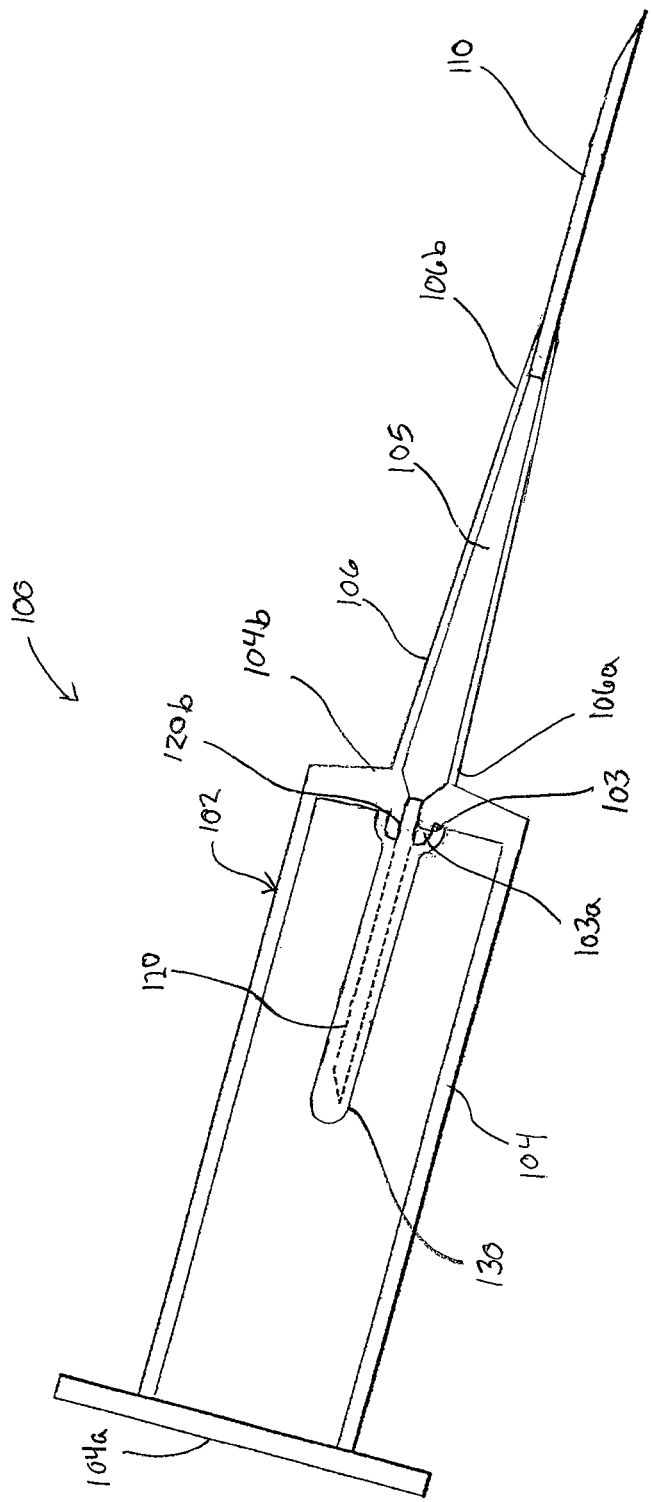
FIG. 1 is a side view of a needle assembly according to the present disclosure.
Figure 2:
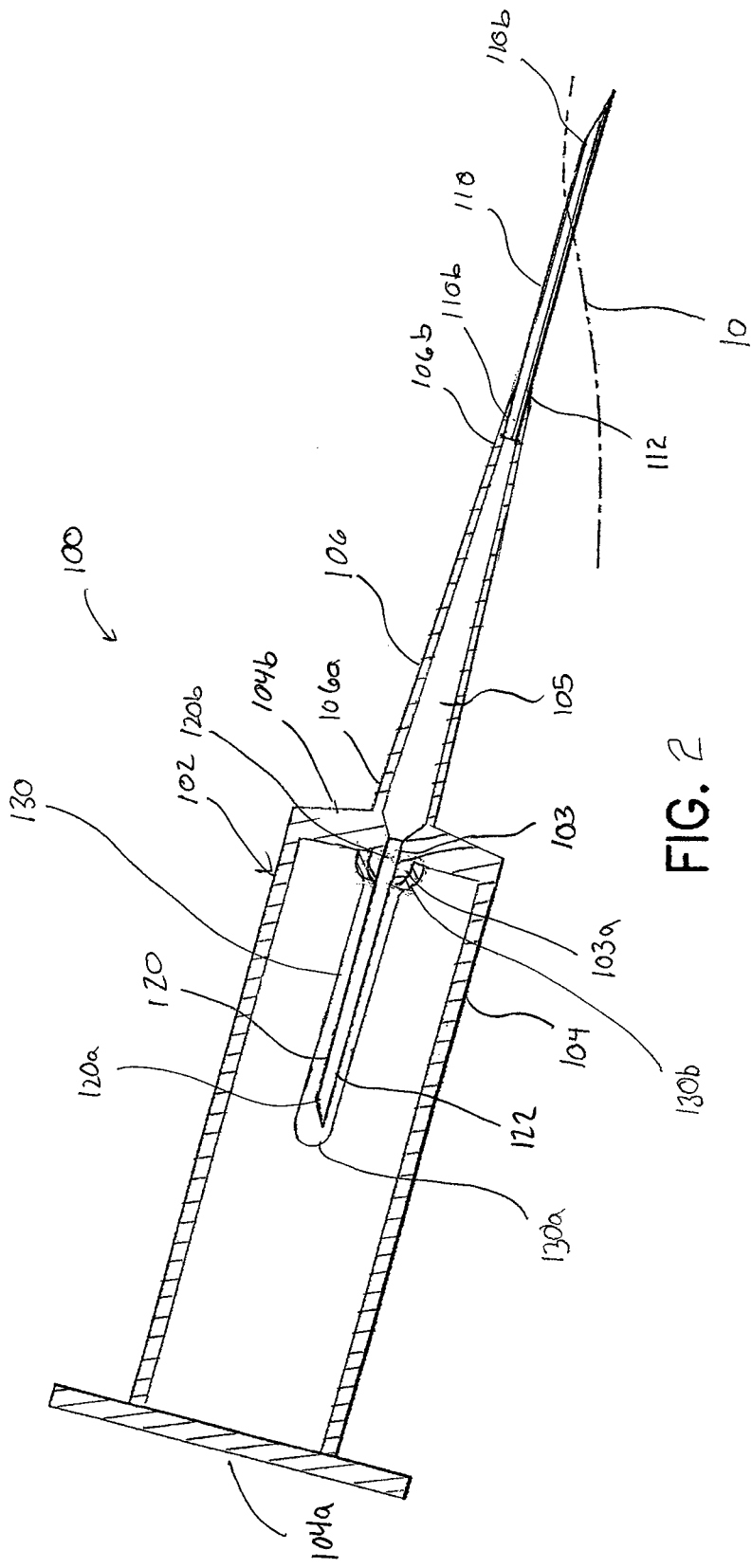
FIG. 2 is a side cross-sectional view of the needle assembly of FIG. 1.

The present disclosure provides a needle assembly for blood collection that provides a visual indication of vein entry ("flashback") without the need for venting the needle assembly. Referring initially to FIGS. 1 and 2, a needle assembly of the present disclosure is shown generally as needle assembly 100. Needle assembly 100 includes a housing 102 having a base portion 104 and extension 106. As will be discussed in further detail below, extension 106 defines a lumen 105 and is transparent, translucent or otherwise configured to permit viewing of the contents of lumen 105. Needle assembly 100 further includes first and second cannulas 110, 120. First cannula 110 is configured for facilitating vein entry during a blood collection procedure. Second cannula 120 is configured for fluid communication with a vacuum tube 50 (FIG. 3) or other fluid receptacle.

Needle assembly 100 includes housing 102 having base portion 104. Base portion 104 defines a substantially cylindrical body configured for receiving vacuum tube 50 (FIG. 3) or other fluid receptacle. Base portion 104 includes a substantially open proximal end 104a and a substantially closed distal end 104b. Distal end 104b of base portion 104 defines an opening 103 configured to support distal end 120b of second cannula 120 therein. Opening 103 may include a flange or other protrusion 103a for further supporting second cannula 120 in fluid communication with opening 103. Flange 103a may further be configured for operable engagement with an elastomeric valve 130. Base portion 104 may be constructed of plastic, glass, metal or other suitable material.

Housing 102 further includes extension 106 which extends distally from base portion 104. As noted above, extension 106 is transparent, translucent or otherwise configured to permit viewing of the contents of lumen 105. Extension 106 may be constructed of plastic, glass or other suitable material. Extension 106 may be constructed of the same material as base portion 104, however, it is envisioned that base portion 104 and extension 106 may be constructed of different materials. As shown, extension 106 is integrally formed with base portion 104 and includes open proximal and distal ends 106a, 106b to define a lumen 105 therethrough. Extension 106 defines a substantially tapered body, wherein proximal end 106a is larger than distal end 106b. Proximal end 106a is integrally formed with base portion 104 and is configured to fluidly communicate lumen 105 with opening 103 formed in distal end 104b of base portion 104. Distal end 106b of extension 106 is configured to support proximal end 110a of first cannula 110. Extension 106 may be configured as a cylindrical lens to magnify the contents of lumen 105, thereby permitting greater visualization of the "flashback" upon vein entry. In one embodiment, the diameter of extension 106 increases in a proximal direction to enhance visualization of "flashback".

First cannula 110 may be constructed of any known material suitable for piercing a vein, i.e., stainless steel. First cannula 110 includes proximal and distal ends 110a, 110b and defines a lumen 112 extending the length thereof. Proximal end 110a of first cannula 110 is configured to be supported within distal end 106b of extension 106 and may include a flange or groove for more securely attaching first cannula 110 within distal end 106b of extension 106. It is envisioned that proximal end 110a of first cannula 110 may be flared or beveled to receive distal end 106b of extension 106 therein. In this manner, proximal end 110a of first cannula 110 supports distal end 106b of extension 106. Distal end 110b of first cannula 110 defines a piercing tip configured for penetrating a vein 10 (FIG. 2). It is further envisioned that proximal end 110a of first cannula 110 may be configured to be threadingly received within corresponding threads formed in distal end 106b of extension 106. In this manner, first cannula 110 may be replaced with a piercing cannula of a different configuration more suitable for a given procedure.

Figure 3:
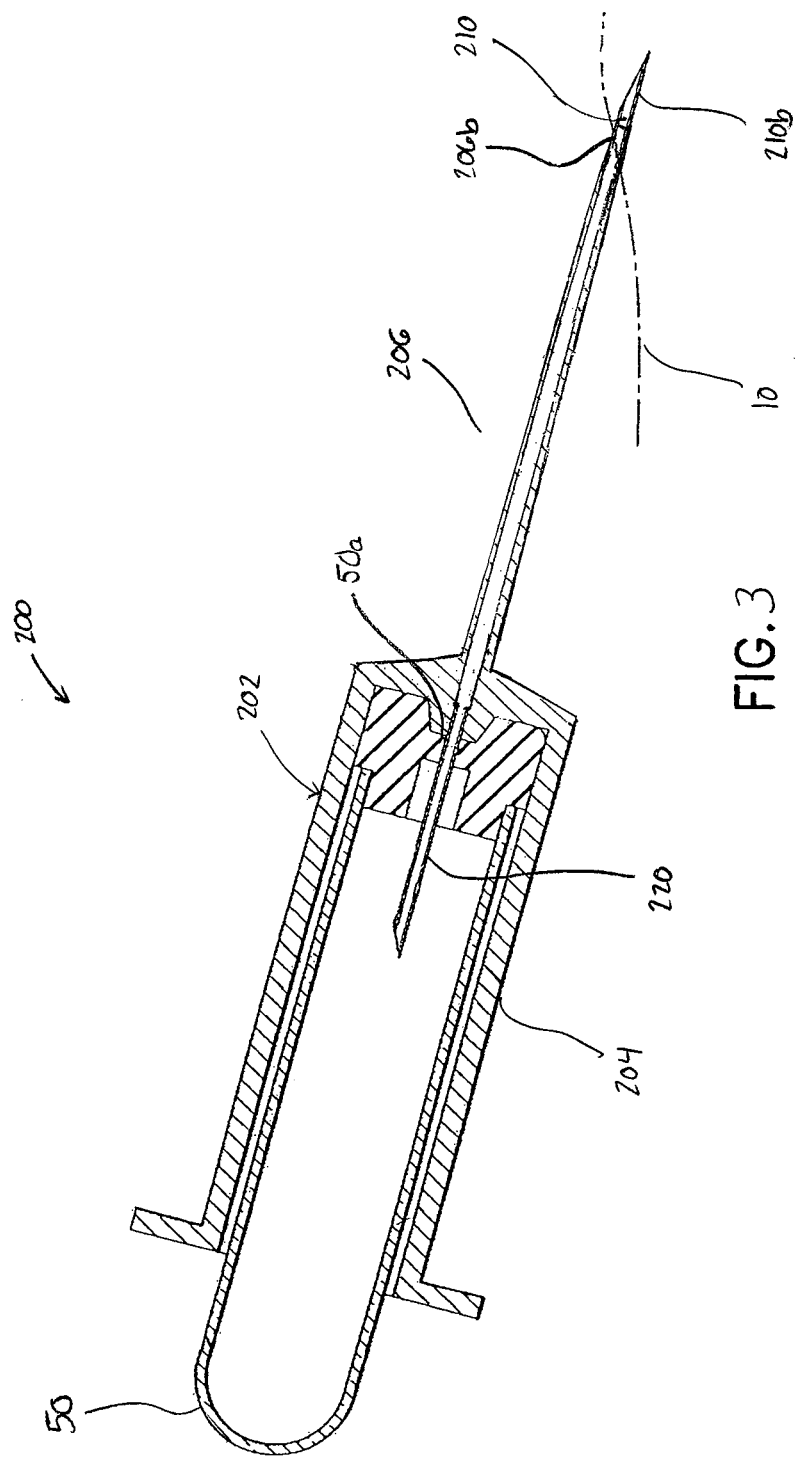
FIG. 3 is a side cross-sectional view of another embodiment of a needle assembly according to the present disclosure.

Needle assembly 100 further includes second cannula 120. Second cannula 120 may be constructed of metal, polymer or any other suitable material. Second cannula 120 includes proximal and distal ends 120a, 120b and defines a lumen 122 extending the length thereof. Distal end 120b of second cannula 120 is configured to be supported within opening 103 formed in distal end 104b of base portion 104 and may include a flange or groove for more secure attachment within opening 103. Distal end 120b may further be configured to engage flange 103 formed in distal end 104b of base portion 104. Proximal end 120a of second cannula 120 defines a tip capable of penetrating sleeve 130 and a septum 50a of vacuum tube 50 (FIG. 3). Second cannula 120 may be of any length and may define lumen 122 of any diameter.

Needle assembly 100 may further include an elastomeric valve or sleeve 130 extending over second cannula 120. Elastomeric valve 130 is substantially similar to known elastomeric valves incorporated into present needle collection assemblies. Elastomeric valve 130 is configured to permit the filling of multiple vacuum tubes 50 during a single blood collection procedure. Elastomeric valve 130 seals cannula 120 when vacuum tube 50 is not operably engaged with base portion 104. As vacuum tube 50 is inserted into base portion 104, elastomeric valve 130 retracts, thereby exposing cannula 120 and permitting the flow of blood into vacuum tube 50. When vacuum tube 50 is removed from base portion 104, valve 130 returns to its original configuration to seal second cannula 120.

During a blood collection procedure using needle assembly 100, a clinician prepares a patient in the usual manner. Once the puncture site has been identified and the area sterilized, the clinician may remove needle assembly 100 from within its sterile packaging (not shown). Distal end 110b of first cannula 110 is used to pierce through the skin and enter into vein 10. Upon entry of first cannula 110 into vein 10 and prior to venting of needle assembly 100, a modest amount of blood will flow into cannula 110. Distal end 106b of extension 106 should be positioned near a distal end of first cannula 110 such that the modest amount of blood flow into cannula 110 prior to venting is visible in distal end 106b of extension 106. More specifically, the length of first cannula 110 must be short enough to allow the modest amount of blood flow which enters cannula 110 prior to venting of needle assembly 100 to flow into extension 106. In this manner, the clinician is able to immediately visualize the "flashback" as the blood travels through first cannula 110 and enters lumen 105. Thus, the clinician does not have to vent the needle assembly 100, such as by inserting a vacuum tube 50 into base portion 104, to confirm that a vein has been entered. In the event the clinician has missed vein 10, no "flashback" will be immediately apparent, thereby signaling to the clinician that a second attempt at puncturing the vein is necessary. In one embodiment, cannula 110 should be no greater than 2 cm in length. It is appreciated that the maximum length of cannula 110 will very depending on the gage thereof.

Insertion of vacuum tube 50 within base portion 104 causes elastomeric valve 130 to retract about second cannula 120. Retraction of elastomeric valve 130 permits the flow of blood through second cannula 120 and into vacuum tube 50. Once vacuum tube 50 has been filled, it may be removed from within base portion 104 and replaced by an empty vacuum tube. After removal of a vacuum tube 50 from base portion 104, elastomeric valve 130 covering second cannula 120 prevents blood from flowing out open proximal end 120a of second cannula 120. Any number of vacuum tubes 50 may be filled in this manner. Once the desired number of vacuum tubes 50 has been filled, first cannula 110 of needle assembly 100 may be withdrawn from vein 10. Needle assembly 100 may then be disposed of in a sanitary manner.

Referring now to FIG. 3, an alternate embodiment of the present disclosure is shown as needle assembly 200. Needle assembly 200 is substantially similar to needle assembly 100, and will only be described with regards to the differences therebetween. Needle assembly 200 includes a housing 202 having a base portion 204 and an extension 206. Extension 206 defines an elongated tubular body having a substantially uniform diameter. Needle assembly 200 further includes a first cannula 210 and a second cannula 220. A distal end 206b of extension 206 is configured to support first cannula 210. First cannula 210 extends from within distal end 206b of extension 206 and forms a piercing tip 210b for penetrating vein 10. Distal end 206b is further configured for insertion into vein 10. In this manner, cannula 210 need only be of a length sufficient to pierce vein 10. As shown in FIG. 3, distal end 206b of translucent extension 206 extends within vein 10. As such, flashback can be visualized immediately adjacent the skin surface despite the fact that only a modest amount of flashback enters the first cannula 210 prior to venting. It is envisioned that extension 206 may be formed to include a piercing distal end 206b, thereby eliminating the need for first cannula 210. Piercing distal end 206b can be formed on extension 206 such as by micro-molding fine beveled geometries using known molding techniques. Alternately, other known techniques can be used.

Turning now to FIGS. 4 and 5, another embodiment of the present disclosure is shown as needle assembly 300. Unlike needle assemblies 100, 200 described herein above, extension 306 is not integrally formed with a base portion (not shown). Instead, extension 306, including first and second cannulas 310, 320, is operably engageable with a base portion. In this manner, needle assembly 300 may be removed from the base portion after use. Because blood only flows through needle assembly 300, the base portion never comes into contact with the collected fluid, and may, therefore, be reused. Needle assembly 300 may be configured for use with any known base portion. Needle assembly 300 may include any of the above disclosed features, including elastomeric valve 130 and a magnifying extension.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A needle assembly comprising:
   a housing including a base portion defining a cavity and an extension extending distally from the base portion, the extension including a transparent material and defining a lumen therethrough; and
   a first cannula supported within the extension and extending distally from the extension, the first cannula having a piercing tip configured to pierce skin and enter a vessel,
   wherein a distal end of the extension is configured for insertion into the vessel such that flashback entering the first cannula prior to venting the needle assembly can be visualized in the lumen of the extension immediately adjacent the skin.

2. A needle assembly according to claim 1, wherein the cavity of the base portion is configured to receive a vacuum tube.

3. A needle assembly according to claim 1, wherein the extension is configured to magnify contents therein.

4. A needle assembly according to claim 1, further including a elastomeric valve operably connected to the base portion and covering the second cannula.

5. A needle assembly according to claim 1, wherein the base portion is integrally formed with the extension.

6. A needle assembly according to claim 1, wherein the extension is operably connected to the base portion.

7. A needle assembly according to claim 1, wherein the transparent extension defines a single lumen.

8. A needle assembly according to claim 1, wherein the lumen formed in the extension defines a substantially uniform diameter along the length thereof.

9. A needle assembly according to claim 1, wherein the extension defines an elongated tubular body having a substantially uniform diameter along the length thereof.

10. A needle assembly according to claim 1, wherein the extension defines a substantially tapered body, wherein a proximal end of the extension defines a larger diameter than a distal end thereof.

11. A needle assembly for permitting viewing of flashback, the needle assembly comprising:
    an elongated body having proximal and distal ends and defining a first lumen therethrough, the body including a transparent material; and
    a first cannula operably supported on the distal end of the elongated body and defining a second lumen in fluid communication with the first lumen, the first cannula having a piercing tip configured to pierce skin and enter a vein,
    wherein the first cannula has a short preselected length and the distal end of the body is configured for insertion into the vein such that upon insertion into the vein, flashback can be visualized in the elongated body immediately adjacent the skin.

12. A needle assembly according to claim 11, further including a second cannula operably supported near the proximal end of the elongated body and defining a third lumen in fluid communication with the first lumen.

13. A needle assembly according to claim 11, wherein the first cannula is no longer than 2 cm.

14. A needle assembly according to claim 12, wherein the first, second, and third lumens are of substantially equal diameter.

15. A needle assembly according to claim 1, wherein the extension remains fixedly attached to the first cannula during use of the needle assembly.

16. A needle assembly according to claim 11, wherein the elongated body remains stationary with respect to the first cannula during use of the needle assembly.

17. A needle assembly comprising:
    a housing including a base portion defining a cavity and an extension extending distally from the base portion, the extension including a transparent material and defining a lumen therethrough, the extension having a piercing tip configured to pierce skin and enter a vessel,
    wherein a distal end of the extension is configured for insertion into the vessel such that flashback entering the extension prior to venting the needle assembly can be visualized in the lumen of the extension immediately adjacent the skin.

* * * * *